(12) United States Patent
Thiel et al.

(10) Patent No.: US 9,681,931 B2
(45) Date of Patent: Jun. 20, 2017

(54) MOLDED MEMBER MADE OF FORM-STABILIZED MATERIAL AND METHOD FOR THE MANUFACTURE THEREOF

(71) Applicant: VITA ZAHNFABRIK H. RAUTER GMBH & CO. KG, Bad Sackingen (DE)

(72) Inventors: Norbert Thiel, Bad Sackingen (DE); Olivia Albarski, Aarau (CH); Michael Dorn, Burladingen (DE); Stefan Aechtner, Bad Sackingen (DE); Joachim Bibus, Bad Sackingen (DE); Andreas Schmid, Bad Sackingen (DE)

(73) Assignee: Vita Zahnfabrik H. Rauter GmbH & Co., KG, Bad Sackingen (DE)

( * ) Notice: Subject to any disclaimer, the term of this patent is extended or adjusted under 35 U.S.C. 154(b) by 554 days.

(21) Appl. No.: 14/106,990

(22) Filed: Dec. 16, 2013

(65) Prior Publication Data
US 2014/0106308 A1  Apr. 17, 2014

Related U.S. Application Data

(62) Division of application No. 12/737,495, filed as application No. PCT/EP2009/059344 on Jul. 21, 2009, now Pat. No. 8,632,889.

(30) Foreign Application Priority Data

Jul. 21, 2008 (EP) ..................................... 08160834
Oct. 28, 2008 (WO) ................. PCT/EP2008/064602

(51) Int. Cl.
A61C 13/08 (2006.01)
A61C 13/00 (2006.01)
A61K 6/02 (2006.01)

(52) U.S. Cl.
CPC ........ *A61C 13/081* (2013.01); *A61C 13/0004* (2013.01); *A61C 13/0022* (2013.01);
(Continued)

(58) Field of Classification Search
CPC . A61C 13/081; A61C 13/0004; A61C 13/082; A61C 13/0022; A61K 6/0255; Y10T 428/24521; B29C 43/006
(Continued)

(56) References Cited

U.S. PATENT DOCUMENTS 1,599,084 A * 9/1926 Gibson ................ A61C 13/081
264/113
2,677,150 A * 5/1954 Rydin .................. A61C 13/081
264/162
(Continued)

FOREIGN PATENT DOCUMENTS

EP  0 455 854  11/1991
EP  0631995  1/1995
(Continued)

*Primary Examiner* — Galen Hauth
(74) *Attorney, Agent, or Firm* — Jacobson Holman PLLC

(57) ABSTRACT

Molded member made of form-stabilized material, comprising at least one first component and one second component, characterized in that the second component has a different pigmentation than the first component and the second component is disposed inside the first element, forming a boundary surface, in such a way that the boundary surface represents a spatially curved surface.

16 Claims, 4 Drawing Sheets

(52) U.S. Cl.
CPC .......... *A61C 13/082* (2013.01); *A61K 6/0255* (2013.01); *Y10T 428/24521* (2015.01)

(58) Field of Classification Search
USPC ......................................................... 264/20
See application file for complete search history.

(56) References Cited

U.S. PATENT DOCUMENTS

| | | | |
|---|---|---|---|
| 4,960,733 A | 10/1990 | Kasuga et al. | |
| 4,970,032 A * | 11/1990 | Rotsaert | A61C 13/0003 264/139 |
| 5,106,303 A | 4/1992 | Oden et al. | |
| 5,614,330 A | 3/1997 | Panzera et al. | |
| 5,775,912 A | 7/1998 | Panzera et al. | |
| 5,849,068 A | 12/1998 | Hofmann et al. | |
| 5,916,498 A | 6/1999 | Hofmann et al. | |
| 5,944,884 A | 8/1999 | Panzera et al. | |
| 6,126,732 A | 10/2000 | Hofmann et al. | |
| 6,354,836 B1 | 3/2002 | Panzera et al. | |
| 6,379,593 B1 | 4/2002 | Datzmann et al. | |
| 6,455,451 B1 | 9/2002 | Brodkin et al. | |
| 6,554,615 B1 | 4/2003 | Brodkin et al. | |
| 6,706,654 B2 | 3/2004 | van der Zel | |
| 6,802,894 B2 | 10/2004 | Brodkin et al. | |
| 6,878,456 B2 | 4/2005 | Castro et al. | |
| 7,091,142 B2 | 8/2006 | Assmann et al. | |
| 7,294,392 B2 | 11/2007 | Aechtner et al. | |
| 2002/0155412 A1 | 10/2002 | Panzera et al. | |
| 2002/0198093 A1 | 12/2002 | van der Zel | |
| 2004/0081847 A1 | 4/2004 | Aechtner et al. | |
| 2004/0121894 A1 | 6/2004 | Brodkin | |
| 2004/0137399 A1 | 7/2004 | Freischfresser | |
| 2004/0232576 A1 | 11/2004 | Brodkin et al. | |
| 2006/0105297 A1 | 5/2006 | Knapp et al. | |
| 2007/0056467 A1 | 3/2007 | Panzera | |

FOREIGN PATENT DOCUMENTS

| | | |
|---|---|---|
| EP | 0 870 479 | 10/1998 |
| EP | 1253116 | 10/2002 |
| JP | 1-145064 | 6/1989 |
| JP | H0723986 | 1/1995 |
| JP | 08-119669 | 5/1996 |
| JP | 11-314938 | 11/1999 |
| JP | 2003-12384 | 1/2003 |
| JP | 2003-048770 | 2/2003 |
| WO | WO 02/09612 | 2/2002 |
| WO | WO 2008/083358 | 7/2008 |

* cited by examiner

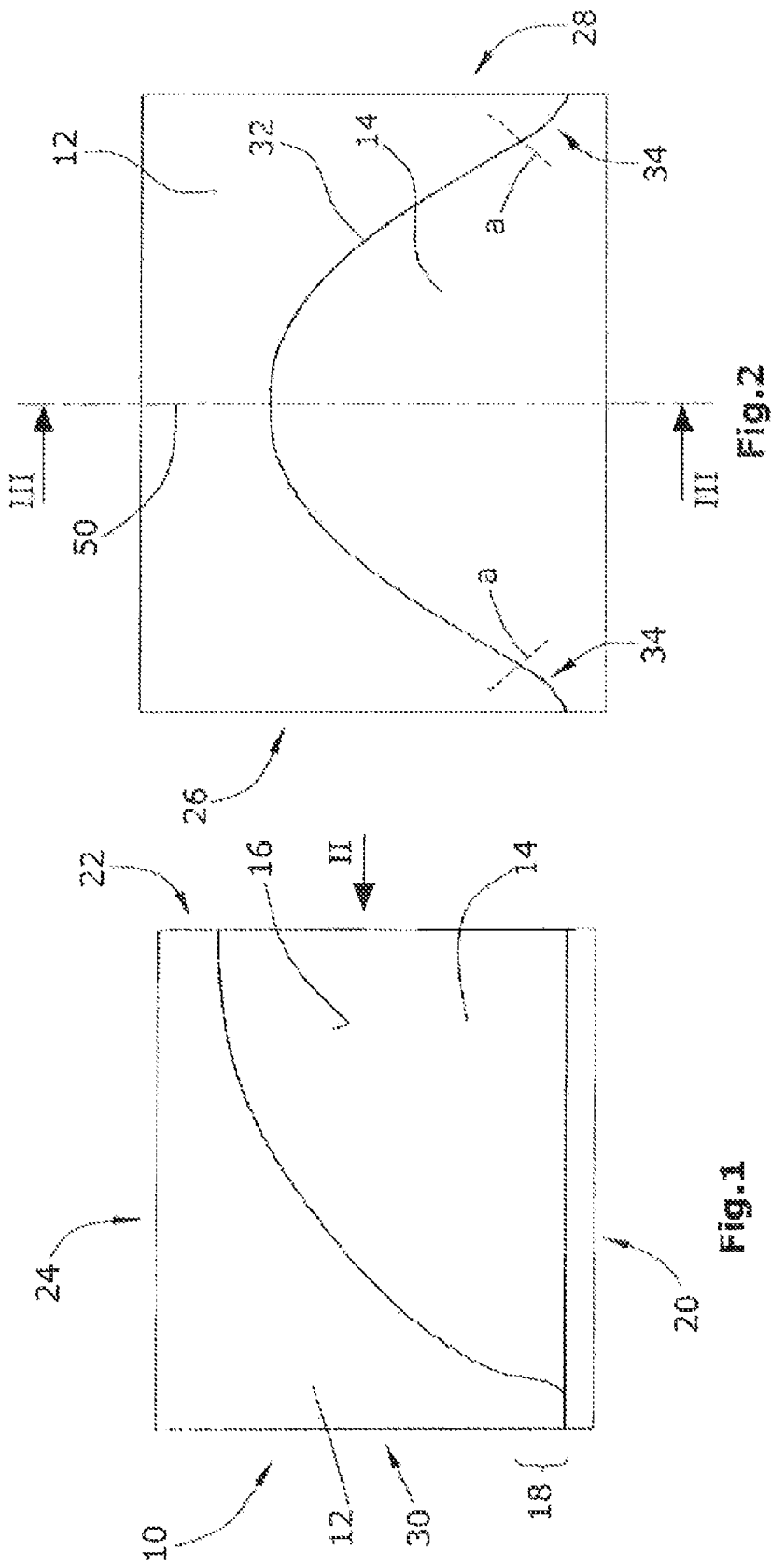

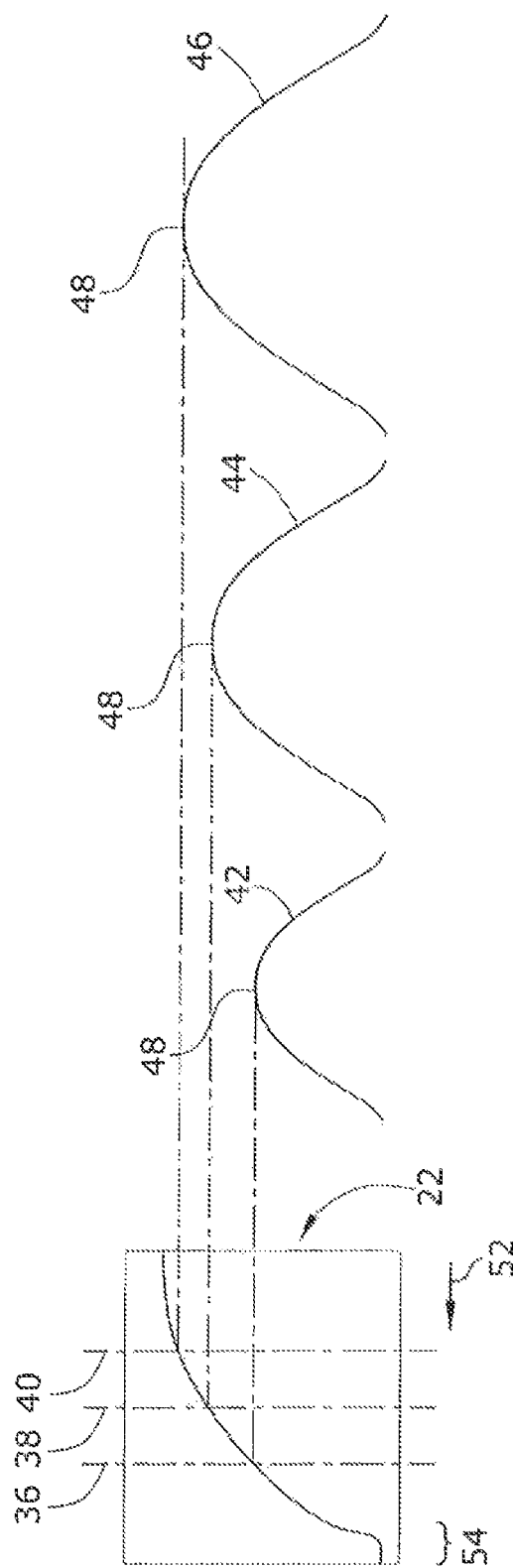

MOLDED MEMBER MADE OF FORM-STABILIZED MATERIAL AND METHOD FOR THE MANUFACTURE THEREOF

This is a divisional of ser. no. 12/737,495, filed, Apr. 18, 2011, which is a 371 of PCT/EP2009/059344, filed Jul. 21, 2009, and which has priority of EP 08 160 834.1, filed Jul. 21, 2008, and PCT/EP2008/064602, filed Oct. 28, 2008 the disclosures of which are incorporated herein by reference.

The present invention relates to a molded member made of form-stabilized material and a process for producing it. The molded member according to the invention is designated, in particular, for use in dental technology.

The preparation of dental prostheses increasingly takes place by machine, employing the CAD/CAM method or the copy milling method, for example. Thus, for example, the dental restoration or a dental crown, inlay, onlay, veneer or a corresponding scaffold are machined from a porous or dense ceramic molded member.

In order to fulfill aesthetic demands and achieve dental restorations with an appearance as close as possible to that of natural teeth, multi-shaded molded members are prepared.

For example, EP-A-455 854 discloses a ceramic molded member made of a usual ceramic or porcelain material with several layers of different colors. The layers can be from glassy transparent in the occlusal area to yellowish opaque in the cervical area.

The disadvantage of the layered/planar structure of the ceramic body as described in EP-A-455 854 is the fact that although it can generate a color gradient similar to that of a natural tooth in a vertical direction, from occlusal to cervical, it cannot in a horizontal direction, which would be of critical importance to aesthetics particularly in the anterior tooth area. In addition, the possible color gradient of the restoration is limited by the thickness/dimension of the layers, which is set already during the production thereof, so that the user is limited in the use of such a block, or a large number of blocks with different layer dimensions must be prepared in order to conform to the natural color gradient of different teeth.

EP-A-870 479 discloses that the color gradient of a dental restoration can be improved and adjusted independently of the starting material in accordance with the high demands on the aesthetics of the dental color image if different starting materials are pressed together. The contact surfaces are subjected to pressure, and the differently colored starting materials are brought into intimate contact in the boundary area, so that mingling, even if only slight, occurs in this area. This mingling, which can be affected by the shape and size of the particles of the starting materials and/or by the pressure applied, enables a flowing color transition to be achieved and means that the actual border between the starting materials is not visible. On the other hand, the pressing process may optionally also be used to produce color regions which are clearly delimited from one another. The use of the pressing process allows both plastic and ceramic to be used as starting materials at low costs, owing to reduced preparation expenditure.

EP-A-870 479 describes the preparation process for blocks with planar layers, wherein the stratification may have a horizontal and/or vertical course. Generally, it is to be noted that the transition between the color layers on the restoration is very abrupt and clearly visible if the restoration has been ground from layered blocks and the interfaces of the color layers emerge on the surface of the restoration. Despite of the mingling described, the course of the interface between the layers is discernible. This also applies to the subject matters of the patent applications described above.

Another drawback of the layered/planar structure of the ceramic body as described in EP-A-870 479 is the fact that it can be used to generate a color gradient only in one direction. When the layers are horizontal in the block, there is a color gradient in the vertical direction in the restoration, i.e., from occlusal to cervical, whereby a color gradient similar to that of a natural tooth can be generated in this direction, but not in a direction perpendicular thereto, i.e., in a horizontal direction, which would be of significant importance to the aesthetic appearance particularly in the anterior tooth area.

When the layers are vertical, a color gradient similar to that of an anterior tooth with respect to the translucent dental enamel in the shape of an arc can be generated if the orientation of the restoration to be ground within the block is chosen accordingly, but only so to a limited extent, since the course depends on the layer dimensions and orientation, and thus a large number of blocks with layers of different thickness must be provided for different cases. In addition, a color gradient equivalent to that of a natural tooth, from occlusal to cervical, can be reproduced only to a limited extent.

WO-A-02/09612 discloses a dental prosthesis comprising a platform adapted to be attached to a milling machine and a piece of material that can be mounted to the platform. The piece of material has plurality of gradations corresponding to different color densities of natural teeth or portions thereof a tooth, the piece of material serving as a dental prosthesis after being processed. The color gradations are to vary gradually like the color gradient of natural teeth, from a lighter to a darker color, where the lighter color corresponds to the enamel and the darker color corresponds to the dentin. It is interesting that this publication already tries to imitate the natural course of the dentin/enamel border. Thus, the skilled person knows what a "natural course of the dentin/enamel border" is supposed to mean, and therefore, this term is by no means unclear.

WO-A-2008/083358 discloses a blank for the preparation of a dental prosthesis that has a different color in an outer zone as compared to an inner zone.

The disadvantage of the blank described in WO-A-2008/083358 is the fact that the inner layers have geometric shapes, cylinders and a rectangular shape, that are arranged concentrically to the outer layers. This limits the number of possibilities for imitating the natural color and translucency gradient of teeth, or although the possible aesthetics of the restoration is higher that that of restorations made from blocks with planar layers, it does not reach the natural model. Also, only a vague description of the shape of the different zones in the block is provided.

The disclosed stratification with more than 2 layers has the same disadvantages as the blocks disclosed in EP-A-455 854 and U.S. Pat. No. 4,970,032. Due to the thickness of the layers, which is determined by the production method, the number of possible restorations is limited.

U.S. Pat. No. 4,970,032 relates to a multi-shaded plastic molded member with predeterminedly varying color layers that are arranged on top of one another around a core. An injection molding method is used for preparing the core and the layers.

U.S. Pat. No. 4,970,032 also discloses a process for preparing artificial teeth by replacing either the whole tooth or by using crowns, wherein the tooth can be prepared by machining a layered block of synthetic rubber material, said block having layers of predetermined color, color appearance and translucency to imitate the pulp, dentin and enamel of a natural tooth to provide an artificial tooth that possesses the color distribution and chroma of a natural tooth.

The plastic block described in U.S. Pat. No. 4,970,032 has a cylindrical central portion surrounded by at least two layers. Thus, there are at least three layers. The invention is based on the concept that the color gradients occurring in natural teeth are to be imitated by differently colored layers in the block. However, there is a disadvantage in that the wide variety of sizes/dimensions of the color layers in natural teeth cannot be reproduced in one block. Due to the dimensions of the layers determined during the production and their course around the cylindrical central portion, the application of the block is limited since it may not be possible to reproduce the required color gradients of the restoration to be prepared despite of different positions of the restoration in the block. Thus, the preparation of several blocks with differently dimensioned layers and layer courses around the cylindrical core is necessary. This is to be observed, in particular, for anterior tooth restorations.

An object to be achieved by the present invention can be seen in providing a molded member enabling an improved appearance of a finished dental restoration and, in particular, enables a wide variety of possible arrangements and designs of the dentin/enamel border. Further, the invention is to provide a process for preparing said molded member.

According to the invention, the technical objects are achieved by a molded member made of form-stabilized material comprising at least a first component and a second component, characterized in that said second component has a different color from that of the first component, and the second component is arranged within the first component to form an interface in such a way that said interface represents a surface curved in space.

In one embodiment, the molded member according to the invention is designed in such a way that the interface at least partially corresponds to the course of the dentin/enamel border of natural or artificial teeth. The colors of the first component and second component are selected so as to come as close as possible to the enamel or dentin color of a natural tooth or artificial tooth. Thus, it becomes possible to provide for a wide variety of courses of the dentin/enamel borders of teeth in the molded member, so that an individual adjustment of the border lines in a dental restoration to be prepared can be effected.

The shape of a molded member according to the invention can be stabilized by different measures. In particular, this can be achieved by mechanical action, especially by pressure, typically within a range of 5-500 MPa, for example, by pressing. Further shaping methods are known to the skilled person. In addition, additive methods, for example, injection molding, may be used for the preparation.

The colors of the components of the molded member according to the invention can be achieved by pigmentation, in the simplest case by means of color pigments, which may at the same time also serve to adjust the translucency. The translucency may also be adjusted by opaquers.

For the use of the molded member according to the invention in dental technology, those molded members whose first and second components are ceramic materials, especially feldspar or oxide ceramic materials, are particularly suitable. However, it is also possible to employ a plastic material. The plastic material may be a thermoplastic material or a thermosetting material. An acrylate-based plastic material is particularly suitable. Suitable plastic materials are known to the skilled person and typically include those used in the preparation of artificial teeth.

First and second components of feldspar ceramic materials comprising metal oxides selected from the group consisting of $SiO_2$, $Al_2O_3$, $Na_2O$, $K_2O$, optionally supplemented by adding pigments and inorganic fillers, may also be used In another embodiment, the components may consist of oxide ceramic materials comprising metal oxides selected from the group consisting of $SiO_2$, $Al_2O_3$, $ZrO_2$ stabilized by various compounds ($Y_2O_3$, $CeO_2$ etc.), optionally supplemented by adding pigments or compounds of colored ions.

In the two described embodiments consisting of feldspar ceramic materials and oxide ceramic materials, the molded member may be either porous-sintered before being further processed, or it may be dense-sintered. It is important to distinguish between the various possible applications, some of which are mentioned in an exemplary manner:

For example, from a dense-sintered feldspar block, a full crown, but also inlays, onlays or veneers, can be ground or milled. In addition, techniques in which dental veneers are ground from dense feldspar or glass ceramic blocks wherein the veneers are sintered onto a scaffold by means of glass solder or adhesively bonded thereon by means of an organic adhesive are already known.

For example, from a porous feldspar material, there can be ground both a crown, wherein the shrinkage of the porous material that occurs when dense-sintered and that may be direction-dependent must be considered during the generation of the grinding data, and a so-called dental veneer, which is put onto a scaffold in a porous state and subsequently fixed, for example, by sintering. The restoration or intermediate products of the final restoration are respectively ground with a bigger size when ground from a porous block. However, when the porous veneer is ground out, it is not necessary to apply the enlarging factor to the whole veneer as is already usual in other methods, for example, the preparation of scaffolds, but in order to avoid cavities, it is advantageous if the interior outline of the veneer and the surface of the scaffold are designed in such a way that they possibly form a mold and a counter-mold, and the enlarging factor is not applied linearly to the veneer.

For example, a scaffold can be ground from a porous oxide ceramic block wherein a color gradient is produced in the scaffold by appropriately positioning the scaffold in the multi-shaded block. After the grinding, the scaffold is dense-sintered if it was previously ground with a bigger size. In the case of infiltration ceramic materials, for example, the scaffold can be ground in a scale of 1:1 and subsequently infiltrated with glass.

In another embodiment of the invention, the molded member according to the invention contains a binder for improving the dimensional stability, especially of the sinterable material. For example, a binder that can be employed is selected from the group consisting of acrylate(s), polyvinyl alcohol (PVA), polyvinyl acetate (PVAC), polysaccharide/acrylic acid (PS/AC), cellulose derivatives or mixtures thereof. Additional auxiliaries, such as water, lubricants for reducing the friction, sintering aids for accelerating the densification, or dispersants, plasticizers, wetting agents and thermoplasts for affecting the rheological properties may be added.

According to the invention, it is particularly advantageous that the second component of the molded member is arranged within the first component. Thus, the first component encloses the second component at least in these areas that are visible after the restoration has been inserted into the patient's mouth. Thus, the second or inner component of the molded member is visible at most before the restoration is inserted into the patient's mouth, in areas facing towards the jaw after the insertion. Thus, the second component is covered by the first component at least in the area that later remains visible. Thus, after the molded member has been inserted, the interface between the two components is no longer visible. After the molded member has been inserted, a stratification cannot be observed. In particular, layer borders cannot be seen.

The embodiment of the molded member according to the invention has the further advantage that different teeth or tooth types can be laid into the molded member in such a way in space that a molded member in which the interface between the two components is arranged within the molded member as above is always obtained. Thus, by means of a single molded member according to the invention, it is possible to imitate a large number of different teeth or tooth types.

In a particularly preferred embodiment, the interface between the first and second components of the molded member, i.e., especially the interface between the material imitating the dentin of a tooth and that imitating the enamel, is essentially described by a family of parabolas. Parallel cross-sectional planes through the molded member can be laid into the molded member in such a way that the boundary between the two components appears as a parabolic border line. In this case, the border line is parabolic through at least ⅔, especially ¾, of its length. Especially the margins or ends of the border line may have a shape differing from that of a parabola, wherein this region of the border line too preferably has no leap or step. In particular, the parabolic border line becomes flatter in the marginal region and is preferably outward oriented.

Over a width of the molded member extending perpendicular to the parallel cross-sectional planes, at least 70% of the cross-sectional planes, especially at least 80% of the cross-sectional planes, have a parabolic border line as defined above.

In an orientation of the molded members in which the second component, i.e., especially the material imitating the dentin, is arranged in the lower portion of the molded member, the parabolas forming the border lines are open towards the bottom. This generates maximums, wherein in a preferred embodiment the parabolas are mirror-symmetrical to a plane extending through the maximums. If the molded member is arranged in this way with dentin facing downward, a plane of symmetry can thus be drawn through all the maximums of the parabolas in a preferred embodiment, In a preferred embodiment, a major cross-sectional plane can be defined which in the position of the molded member with dentin facing downward is the cross-sectional plane in which the parabolic border line has the greatest or highest maximum. Starting from the major cross-sectional plane, the height of the border line preferably decreases continuously in a taper direction. In particular, a curve defined by the maximums decreases continuously at least through a major part of its length of especially more than half and preferably more than ¾ of its length. The connecting curve of the maximums preferably lies in the plane of symmetry and/or is oriented perpendicular to the major cross-sectional plane. Relative to the width of the second component in the taper direction, the decrease of the maximums of the parabola preferably goes through at least 50%, more preferably through at least 75%, of the total length or total width of the second component.

Preferably, both ends of the border line or both ends of the branches of the parabola merge into a curve of opposite curvature. Thus, in a preferred embodiment, the parabolic part of the border line is followed by an outward curve to form a point of inflection.

The above described particularly preferred embodiment of the interface between the first component, which imitates the enamel, in particular, and the second component, which imitates the dentin, in particular, may have slight deviations. This is a geometric approximation, so that deviations of up to 10% are possible. In particular, the design of the border line is effected on the basis of experience and of examinations of the enamel/dentin border in natural and/or artificial teeth.

For preparing an artificial tooth, the molded member can preferably be represented by a suitable computer software and can rotate freely in space, in particular. Thus, a dentist or dental technician can view the border line from different perspectives. The geometric dimensions of the tooth to be reproduced are transmitted to the computer, for example, by image processing programs. The dentist or dental technician can arrange the virtual tooth produced thereby in any position desired within the molded member and thus arrange the interface between the dentin and enamel in such a way that the appearance of impression of the tooth to be prepared later from the molded member corresponds to that of the patient's natural teeth, especially the patient's neighboring teeth, or is at least very similar. Due to the arcuate course in combination with the free positioning of the restoration in the block, it is possible to have not only a (mirror-)symmetrical design of the enamel/dentin border, but also a horizontally asymmetric shape, as usually found in natural teeth. In addition, by appropriately positioning the restoration within the block, a layer of enamel composition that is tapered from occlusal to cervical can be laid over the dentin composition, which generates a color gradient from light to dark that has no horizontal layer borders and corresponds to the natural, non-graded color gradient.

The invention relates to a process for preparing the molded member according to the invention, especially consisting of a sinterable material or plastic material, which has at least one first and at least one second component, wherein
a) said at least one first component is filled into a mold;
b) a depression having a surface is pressed into the filled-in at least one first component of said material, especially sinterable material or plastic material; and
c) said surface forms an interface curved in space towards
d) the at least one second component filled into the depression.

If a plastic material is used for said first and second components, it is cured, in particular, at an elevated temperature and optionally under pressure.

The surface of the interface is designed to correspond at least partially to the course of the dentin/enamel border of natural or artificial teeth.

The preparation of the molded member may also be effected by ceramic injection molding or similar preparation methods.

According to one embodiment of the invention, the construction of the interface is effected by positioning the enamel/dentin interfaces of different natural and/or artificial teeth. In natural teeth, the enamel can be carefully removed in a preparative manner to characterize the position of the interface between the enamel and dentin. In doing so, it is to be taken care that the dentin layer is not ablated. It is easier to prepare artificial teeth and the course of their interface. The course of the interface in artificial teeth mimics the course in natural teeth. In order to prepare members showing this course of the interface, the teeth are not prepared with all the layers, but the more translucent enamel layer is omitted. Thus, after the sintering process, a surface of the artificial tooth is obtained that corresponds to the course of the enamel/dentin interface.

By preparing different teeth, a curved surface corresponding to the course of the interface of the different teeth can be modeled by arranging the different dentin/enamel interfaces in space, preferably by a size-dependent arrangement. From this model, a mold can be prepared.

An alternative possibility of modeling the interface is to digitalize courses of the enamel/dentin interface and to generate the model by a software. This offers the possibility to include a substantially higher number of interface courses in the generation of the interface. In addition, a mold can then be prepared much more easily by means of CAD-CAM methods.

Using the mold, a desired molded member can be prepared. In order to effect a three-dimensional measurement of the molded member or the course of the interface, a molded member is sawed into as large as possible a number of plane-parallel disks, and the disks are ground smooth on both sides.

Before the sawing, a continuous mark, preferably a groove, that connects diagonal corners of the molded member is applied to the molded member perpendicular to the sawing direction, enabling an unambiguous determination of the position of a disk by measuring the position of the groove on the edge of the disk.

By measuring the position of the interface on the disks, a point cloud representing the enamel/dentin interface can be established in a coordinate system.

In the process according to the invention, this can be followed by a sintering step as an intermediate step. This has the advantage that the molded member is more stable.

The molded member according to the invention may also be prepared by correspondingly performed dry or wet processes, such as pressure slip casting.

For example, the preparation process by means of pressure slip casting can be performed as follows:
a.) preparing a molded member A having the geometry of the surface from the above mentioned preparation process by casting a slip, for example, into a porous plaster mold whose surface corresponds to the boundary described, with or without application of pressure;
b.) preparing a second molded member B with a negative contour with respect to molded member A according to a.);
c.) assembling the two molded parts A and B into a compound unit C, possibly with thermal aftertreatment, with or without pressure within or outside a mold (after demolding) that determines the overall outer shape of compound unit C (surface of the assembled component/compound unit).

Or:
a.) preparing a molded member A having the geometry of the surface from the above mentioned preparation process by casting a slip, for example, into a porous plaster mold whose surface corresponds to the boundary described, with or without application of pressure;
b.) demolding molded member A and positioning molded member A in another plaster mold that is to correspond to the final contour of the compound unit;
c.) filling the mold with another slip with or without application of pressure and possibly with thermal aftertreatment within the mold or after demolding.

The preparation process by means of a dry process can be performed as follows:
a.) preparing a molded member A having the geometry of the surface from the above mentioned preparation process by inserting a plasticized composition with or without added binders into a corresponding mold, possibly with thermal stabilization with or without pressure;
b.) preparing a second molded member B with a negative contour with respect to molded member A according to a.);
c.) assembling the two molded parts A and B into a compound unit C, possibly with thermal aftertreatment, with or without pressure within or outside a mold that determines the overall outer shape of compound unit C (surface of the assembled component/compound unit).

The preparation processes described have long been known in principle in the field of ceramic forming (Hülsenberg, Keramikformgebung, ISBN 3-342-00098-8).

The molded member according to the invention can be employed for preparing a dental restoration, which is constructed and prepared, in particular, by CAD/CAM methods.

The invention also relates to a process for preparing a molded member made of form-stabilized material with an interface extending within the molded member, wherein said material has at least a first component and a second component;

said second component has a pigmentation different from that of the first component, and the second component is arranged within the first component to form an interface in such a way that said interface represents a surface curved in space;

said interface is obtainable by creating surfaces having radii of curvature with different degrees of curvature from sections made through a set of natural or artificial teeth; and/or said interface is obtainable by creating surfaces having radii of curvature with different degrees of curvature from courses of the dentin/enamel border of natural or artificial teeth of the set;

the created surfaces having radii of curvature with different degrees of curvature are arranged in space as a function of the degree of curvature of the radii of curvature; and wherein an arrangement in space of the created surfaces resulting therefrom produces the totality of the interface.

In one embodiment of the process according to the invention for preparing the molded member according to the invention with the interface, the marginal region of the courses of the dentin/enamel border can be left unconsidered when the created surfaces are arranged.

In another embodiment, the production of the totality of the interface can consider only those teeth whose dentin/enamel border is in accordance with a predetermined approximating surface to at least 80%, especially at least 90%. In particular, the approximating surface is approximated by significant dentin/enamel borders of natural or artificial teeth.

In still another embodiment of the process according to the invention, the teeth having a great curvature of the dentin/enamel border are combined to form an apical region of the interface, or arranged in the apical region of an approximating surface. For example, the teeth selected to be arranged in the apical region can be sorted essentially by their size.

In another embodiment of the process according to the invention, the teeth having a small curvature of the dentin/enamel border are combined in the marginal region of the interface, or arranged in the marginal region of an approximating surface. In this case too, the teeth selected to be arranged in the marginal region can be sorted essentially by their size.

In another embodiment of the process according to the invention, the teeth having a medium curvature of the dentin/enamel border may be combined to form an intermediate region of the interface arranged between the marginal region and the apical region, or arranged in the intermediate region of an approximating surface. In this case too, the teeth selected to be arranged in the intermediate region can be sorted essentially by their size.

According to the invention, it is also possible to perform the size sorting in the same direction in space independently of the intensity of the curvature.

In the following, a molded member according to the invention is illustrated in preferred embodiments, wherein:

FIG. 1 shows a schematic lateral view of a molded member;

FIG. 2 shows a schematic rear view in the direction of arrow II of the molded member shown in FIG. 1;

FIG. 3 shows a schematic sectional view along the line III-III in FIG. 2;

FIG. 4 shows representations of the border line in different cross-sectional planes defined in FIG. 3;

Figure 5:
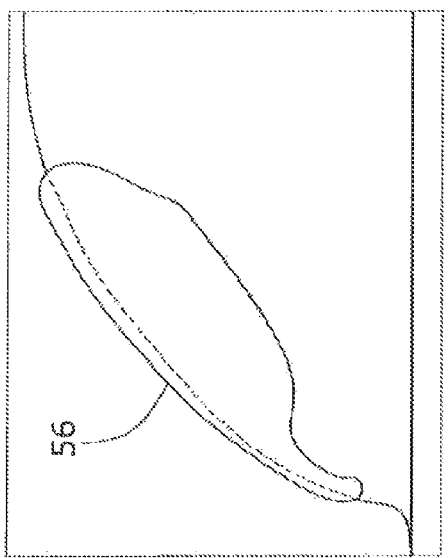
FIG. 5 shows a preferred embodiment of a molded member according to the invention with a schematic representation in a front view of the artificial tooth to be prepared.

In the following, the geometric design of the interface underlying the embodiment of the molded member according to the invention is described by means of FIGS. 1 to 4.

A molded member 10 has a first component 12 and a second component 14. The first component 12 consists of the material imitating the enamel of a tooth. The second component 14 consists of the material imitating the dentin of a tooth. According to the invention, an interface 16 between the two components 12, 14 is designed as a surface curved in space. Mathematically, the interface 16 can be described at least approximately by a family of parabolas. This applies at least to a major part of the cross-sectional area, wherein deviations from the parabolic shape may exist, in particular, in a bottom region 18.

The interface 16 is arranged within the molded member 10 in such a way that the second component 14 forms the whole interface 16 of the cuboid molded member in the example shown (FIG. 2). In the rear view (FIG. 2), in which the lateral exterior surface 22 of the molded member 10 is visible, part of the exterior surface is formed by the second component 14, and the remaining part is formed by the first component 12. An upper exterior surface 24 of the molded member 10 is exclusively formed by the first component 12. The two opposing exterior surfaces 26, 28 (FIG. 2) of the molded member are formed by the first component 12 to a very large part thereof. Only in the lower region, the exterior surfaces 26, 28 are formed by the second component 14. The exterior surface 30 is also formed accordingly (FIG. 1).

From a rear view (FIG. 2), a border line 32 of the interface 16 is visible. The border line 32, i.e., the boundary between the two components 12, 14 is formed in a parabolic shape at least between the two auxiliary lines "a" shown as dashed lines. Beyond the parabolic design, there are ends 34 of the border line 32. These have an outward oriented course, and in the example shown, they involve a change of curvature. Thus, a point of inflection is provided in the end region 34 of the border line 32.

In different cross-sectional planes 36, 38, 40 (FIG. 3), the interface 16 has border lines 42, 44, 46 (FIG. 4), which correspond to the curve 32 (FIG. 2) in their mathematical fundamental structure. Thus, the border lines 42, 44, 46 also have a parabolic design except for their respective ends. The ends in turn are pointing outward and form a point of inflection.

Each parabola of the individual cross-sectional planes 36, 38, 40 has a maximum 48. In the longitudinal section along a plane of symmetry 50 (FIG. 2) as shown in FIG. 3, the curve of the maximums can be seen. The curve of the maximums decreases continuously over the width of the molded member 10 or in the taper direction 52. This holds at least over a major part of the whole length of the curve of the maximums. Optionally, there may be deviations in an end region 54. In the example shown, the maximums of the parabolas decrease from that of a major cross-sectional plane, wherein the major cross-sectional plane corresponds to the exterior plane 22 in the example shown.

FIGS. 5 to 8 show a preferred embodiment of a molded member, which is a virtual molded member represented by means of a computer software, in particular. In principle, the molded member is designed as illustrated above by means of FIGS. 1 to 4 and has a first component 12 and a second component 14. An artificial tooth 56 to be prepared can be embedded in molded member 10 virtually. In doing so, it is possible to arrange the tooth in any position desired in the molded member 10, so that the interface between the two components 12, 14, i.e., the dentin-enamel interface 16, can be laid into the tooth 56. For this purpose, the outer dimensions of the artificial tooth 56 to be prepared are known. For example, these can be selected from predetermined patterns. Also, a three-dimensional representation can be made by including several images of the tooth to be replaced or a neighboring tooth thereof.

Optionally, combinations of virtual tooth patterns with geometric data acquired by image processing can be effected. Optionally, the shape may be processed by a user, such as a dentist or dental technician. In order to achieve an appearance as true to nature as possible, the artificial tooth 56 to be prepared can be arranged in different positions with respect to the interface by the dentist or dental technician. Thus, the first component 12 of the molded member, which imitates the enamel, can have a different thickness in different regions, so that the interface between the two components within the tooth 56 to be prepared approximates the dentin-enamel border of a natural tooth of the patient.

Figure 6:
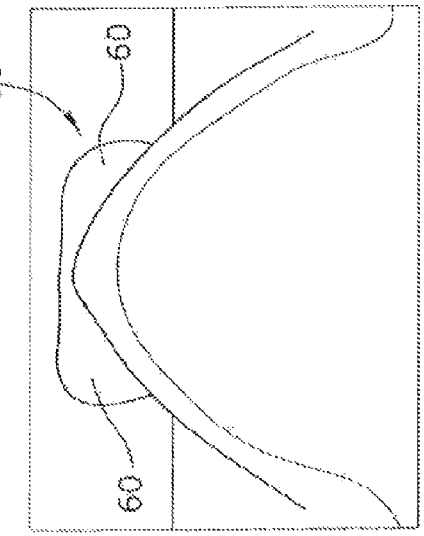
FIG. 6 shows a lateral view of the molded member shown in FIG. 5, the tooth being represented schematically and transparent.
Figure 7:
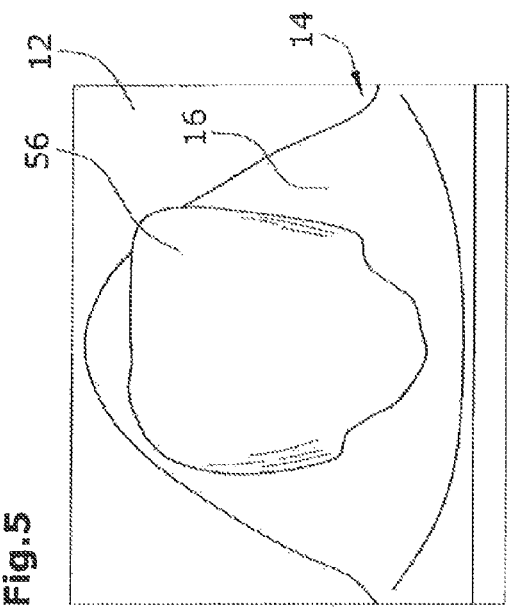
FIG. 7 shows a lateral view corresponding to FIG. 6, the dentin component of the molded member being represented schematically and transparent.
Figure 8:
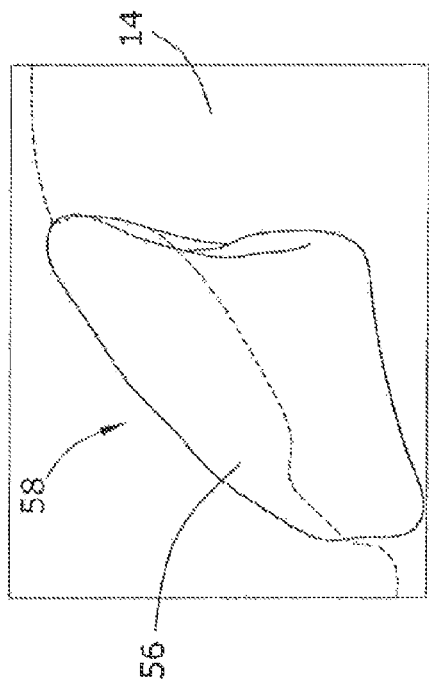
FIG. 8 shows a rear view of the molded member shown in FIG. 5.
Figure 9:
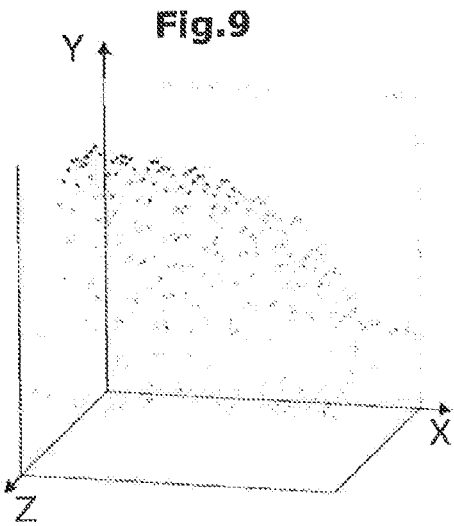
FIG. 9 shows a three-dimensional representation of a coordinate system in which examination results of the dentin/enamel border of natural and artificial teeth are given.
Figure 10:
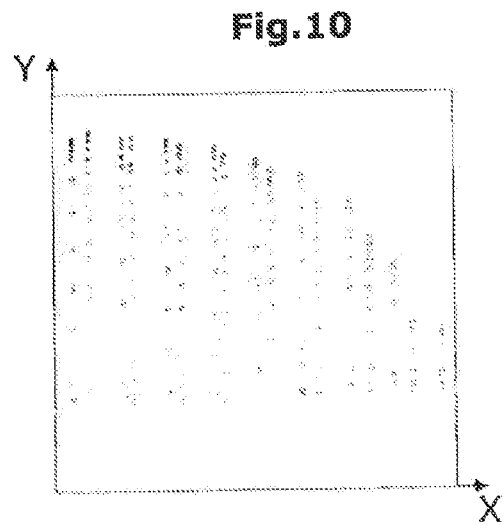
FIG. 10 shows a projection of the representation shown in FIG. 9 onto the X-Y plane.
Figure 11:
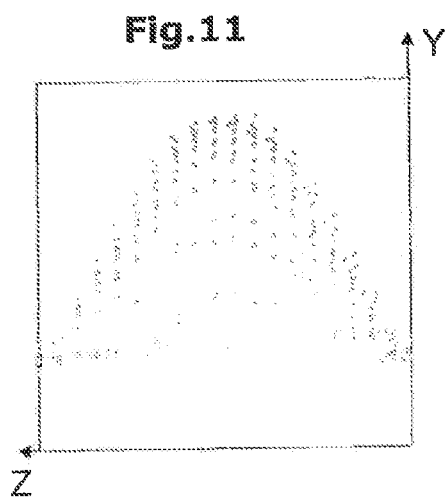
FIG. 11 shows a projection of the representation shown in FIG. 9 onto the Y-Z plane.
Figure 12:
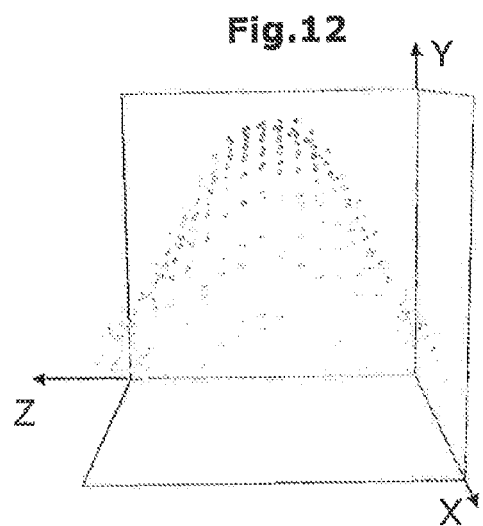
FIG. 12 shows a representation of the examination results according to FIG. 9 with a changed orientation of the coordinate system.

To illustrate the position of the tooth 56 to be prepared, it is represented transparent in FIG. 6. The border line is shown as a dashed line. Further, in FIG. 7, it is shown as a dashed line towards the second component 14 forming the dentin. From this, it can be seen that the whole later anterior side 58 of the tooth 56 to be prepared will be formed by the first component 12, which imitates the enamel. Further, as can be seen from FIG. 8, in particular, regions of the tooth 56 may exclusively consist of the first component 12. These are the regions 60.

In a preferred embodiment, the mathematical approximation explained, in particular, by means of FIGS. 1 to 4 is based on examinations explained by means of FIGS. 9 to 12 in the following. In FIGS. 9 to 12, measuring results are shown by individual circles.

The invention is further illustrated by means of the following examples.

The feldspar granules employed for the experiments described in the following have the following compositions:

| Oxides | Percent by weight |
|---|---|
| $SiO_2$ | 56-64 |
| $Al_2O_3$ | 20-23 |
| $Na_2O$ | 6-9 |
| $K_2O$ | 6-8 |
| CaO | 0.3-0.6 |
| $TiO_2$ | 0.0-0.1 |

Using a graphics software, for example, the software Freeform, the interfaces of the enamel/dentin interfaces of the upper jaw and lower jaw teeth are combined respectively from the right-hand side triplet to the left-hand side triplet, for example, of Vitalife teeth, of pycnic, leptosomal and athletic forms of the teeth to thereby generate the interface shape. Alternatively, the interfaces of natural teeth may be carved out by removing the enamel layer, followed by scanning the surfaces with a commercially available scanner, for example, with a stripe-light scanner, and combined by using the software. Taking into account the shrinkage value known for the granules under the pressing and sintering conditions as described below, which is determined in additional experiments, the arcuate shape is calculated as an enlarged shape using the software, in order that an exact image of the calculated interface is obtained after the block has been completed. The software is used to generate an STL file. The enlarged arcuate shape is prepared from a brass block by means of a CAD/CAM process using a CNC milling machine, wherein a rectangular prism is attached as a guide to the bottom side of the arcuate shape, and serves as a support and guide for the molding plug.

Other possibilities for preparing a molding plug are known to the skilled person.

A first possibility of block preparation is as follows:

In a stainless steel die having interior dimensions 16.6 mm×21 mm matched to the molding plug, the height being 63 mm and the wall thickness being about 10 mm, granulated feldspar material of the translucent outer layer admixed with a commercially available binder is filled. After the molding plug has been inserted, the molding plug is loaded in a press with a force of 1.5 kN, and the granules are prepressed. After the charge has been released from the molding plug and the latter removed, the second granules, which are distinguished from the first, already compacted granules in shade by the addition of correspondingly coloring oxides and which form the enamel, is filled into the enlarged arcuate shape in the green body and a little beyond. A second molding plug with a flat surface is inserted and applied with a load of 1.5 kN, so that the second granules is compressed in a way equivalent to that of the first granules.

Subsequently, the molding plug is removed, and the green body is discharged from the die. The mass of the green body is about 9.5 g.

Another possibility for preparing a block is described in the following, wherein the granules employed are identical with the previous description. Previously, the molding plug is calculated in accordance with the process parameters employed.

1.) Filling the die having a size of 21.0 mm×16.5 mm with an amount of about 5.25 g of material; and lowering the molding plug countering in the die (lower punch) to the filling amount of the translucent color component (dependent on the target height of the cuboid end product and the bulk density), typically 18-35 mm.

2.) Compacting the filled-in composition with a second die whose surface is enlarged over that of the finished block in 3 directions of space, so that the compacted material remains dimensionally stable in the die, typically in such a way that the distance between the second die and the lower punch is between 14 and 25 mm. The amount of material to be compressed and the distance between the punches determines the density of the precompacted dimensionally stable molded member.

3.) Filling the precompacted dimensionally stable mold with the darker material according to the target height of the end product according to 1.) to be achieved, typically 4.25 g.

4.) Compacting the compound unit to a specific final density of typically 1.54 g/cm$^3$ (here 22.4 kN) to a height of typically 16.7 mm, so that the final molded member is dimensionally stable. The pressing pressure/force depends on the material and process parameters.

5.) Demolding the compound unit from the die.

From the thus obtained blocks, consisting of a light translucent outer layer and a dark opaque inner layer, the binder is removed in accordance with the binder employed. This process is known to the skilled person and depends on the binder employed and the selected grain size of the ceramic material. After the removal of the binder at 700° C. to 800° C., the now obtained porous block is dense-sintered under vacuum at about 1200° C., so that pores and cavities are no longer present. After the dense-sintering, a fixture for a Cerec grinding machine from Sirona is applied to the block, in order that the block can be ground in the machine. By a corresponding software, which enables the rotation as well as the translational movement of the restoration within the block, a freely selectable position of a restoration in the block with an individual course of the enamel/dentin interface can be prepared.

The invention claimed is:

1. A process for preparing a molded form-stabilized member comprising the steps of
    a) filling a mold with the at least one first component comprising a pigmentation,
    b) compressing the at least one first component in the mold to form in the at least one first component a depression having a surface curved in space,
    c) filling the depression with at least one second component comprising a different pigmentation than the first component, and
    d) compressing the at least one second component in the depression, such that the surface curved in space forms an interface, curved in space towards the at least one second component, between the at least one first and second components, thereby producing the molded form-stabilized member, wherein the interface (16) is essentially described by a family of parabolas, whereby the second component (14) has an essentially parabolic border line (42, 44, 46) towards the first component in a cross-sectional plane (36, 38, 40), wherein continuously decreasing maximums (48) go through at least 50% of the second component (14) in a taper direction (52), Wherein the second component (14) respectively has an essentially parabolic border line (42, 44, 46) in all mutually parallel cross-sectional planes (36, 38, 40), and wherein the essentially parabolic border lines (42, 44, 46) have continuously decreasing maximums (48), starting from a major cross-sectional phase (22) in the taper direction (52) and extending perpendicular to the major corss-sectional plane (22).

2. The process according to claim 1, wherein (i) each of the first and second components further comprises sinterable ceramic material or (ii) each of the first and second components further comprises plastic material.

3. The process according to claim 2 further comprising, after the filling and compressing step (c), the step of curing the first and second components at an elevated temperature under pressure, when each of the first and second components further comprises plastic material.

4. The process according to claim 1, wherein the interface constitutes a surface at least partially corresponding to a course of the dentin/enamel border of natural or artificial teeth.

5. The process according to claim 2 further comprising, after the filling and compressing step (c), the step of sintering the first and second components, when each of the first and second components further comprises sinterable ceramic material.

6. In a process of making a dental restoration comprising working a dental-restoration material, the improvement wherein the dental restoration material is a molded form-stabilized member produced by the process of claim 1.

7. The process of claim 6, wherein the dental-restoration material is worked by CAD/CAM methods.

8. The process of claim 1
wherein the interface is constituted by at least partially corresponding to a section made through a set of natural or artificial teeth.

9. The process according to claim 8, wherein the course of the dentin/enamel border is in at least 80% accordance with the interface.

10. The process according to claim 1, wherein the pigmentation and different pigmentation serve to adjust at least one of translucency and color of the first and second components.

11. The process according to claim 1, wherein each of the pigmentation and different pigmentation comprises a translucency adjusting opaquer.

12. The process according to claim 1, wherein each of the pigmentation and different pigmentation further comprises a color adjusting pigment.

13. The process according to claim 1, wherein the continuously decreasing maximums (48) go through at least 75% of the second component (14) in the taper direction (52).

14. The molded member according to claim 1, wherein the continuously decreasing maximums (48) lie in a common plane (50) extending in the taper direction (52).

15. The molded member according to claim 1, wherein the continuously decreasing maximums (48) lie in a common plane (50) extending in the taper direction (52), wherein the common plane (50) is a plane of symmetry for the second component (14).

16. The molded member according to claim 1, wherein at least one end (34) of the essentially parabolic border line (42, 44, 46) merges into a curve of opposite curvature.

* * * * *